(12) United States Patent
Lee et al.

(10) Patent No.: US 6,306,629 B1
(45) Date of Patent: Oct. 23, 2001

(54) MICROORGANISM STREPTOMYCES EXFOLIATUS YJ-118 AND A METHOD FOR PRODUCING PRAVASTATIN SODIUM BY USING THE STRAIN

(75) Inventors: Joo-Kyung Lee; Joo-Woong Park, both of Seoul; Dong-Jin Seo, Kyungki-do; Sang-Choon Lee, Seoul; Ji-Yoon Kim, Kyungki-do, all of (KR)

(73) Assignee: Yungjin Pharmaceutical Ind. Co., Ltd. (KR)

( * ) Notice: Subject to any disclaimer, the term of this patent is extended or adjusted under 35 U.S.C. 154(b) by 0 days.

(21) Appl. No.: 09/402,784

(22) PCT Filed: Jun. 20, 1997

(86) PCT No.: PCT/KR97/00130

§ 371 Date: Dec. 29, 1999

§ 102(e) Date: Dec. 29, 1999

(87) PCT Pub. No.: WO98/45410

PCT Pub. Date: Oct. 15, 1998

(30) Foreign Application Priority Data

Apr. 10, 1997 (KR) .................................................. 97-13290

(51) Int. Cl.$^7$ ........................................................ C12P 7/62
(52) U.S. Cl. .......................... 435/135; 424/121; 424/305; 435/125; 435/169; 435/252.1; 435/253.5; 544/292; 549/292; 560/119; 560/188; 560/256
(58) Field of Search ..................................... 424/121, 305; 435/125, 135, 169, 252.1, 253.5; 544/292; 549/292; 560/119, 188, 256

(56) References Cited

U.S. PATENT DOCUMENTS 5,153,124 * 10/1992 Furuya et al. ........................ 435/125
5,332,574 * 7/1994 Sugawara et al. ................... 424/121

* cited by examiner

*Primary Examiner*—Francisco Prats
*Assistant Examiner*—K. C. Srivastava
(74) *Attorney, Agent, or Firm*—Finnegan, Henderson, Farabow, Garrett & Dunner, L.L.P.

(57) ABSTRACT

The present invention is related to a new microorganism Streptomyces exfoliatus YJ-118 and a method for producing pravastatin sodium by using this microorganism which shows a strong tolerance to ML-236B and a high hydroxylation activity of ML-236B to pravastatin.

4 Claims, 3 Drawing Sheets

MICROORGANISM STREPTOMYCES EXFOLIATUS YJ-118 AND A METHOD FOR PRODUCING PRAVASTATIN SODIUM BY USING THE STRAIN

BACKGROUND OF THE INVENTION

1. Field of the Invention

The present invention is related to a new microorganism *Streptomyces exfoliatus* YJ-118 and a method for producing pravastatin sodium represented in formula I by using this microorganism which shows a strong tolerance to ML-236B and a high hydroxylation activity of ML-236B to pravastatin.

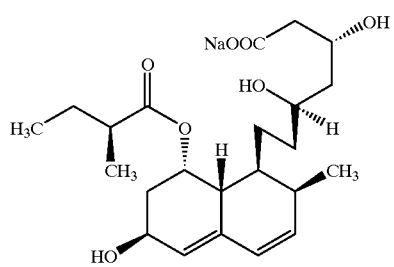

(I)

2. Description of the Prior Art

An elevated plasma cholesterol level has long been recognized as a major risk factor for atherosclertic disease, and specifically for coronary heart disease. It was expected that plasma cholesterol could be reduced as a result of inhibition of cholesterol biosynthesis because more than 70% of the total input of body cholesterol is derived from de novo synthesis in humans. In 1975, ML-236B, a potent inhibitor of 3-hydroxy-3-methylglutaryl coenzyme A (HMG-Co A) reductase, a rate-limiting enzyme in the biosynthesis of cholesterol, was discovered in the culture broth of Penicillin citrium. After thorough screening of hundreds of microbial products as well as chemically or biologically modified derivatives of ML-236B, pravastatin sodium was chosen as a candidate for development, because of its stronger and more tissue-selective activity than the prototype compound.

Pravastatin has been produced by two-step fermentation: first, biosynthesis of ML-236B and second, bioconversion of this compound to pravastatin sodium. Lactone and carboxylate of ML-236B are represented in formula II-a and formula II-b, respectively.

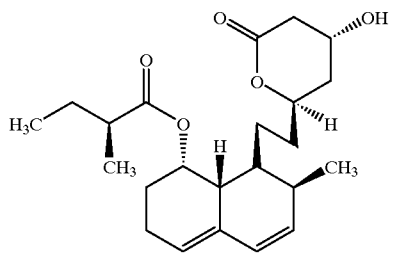

(II-a)

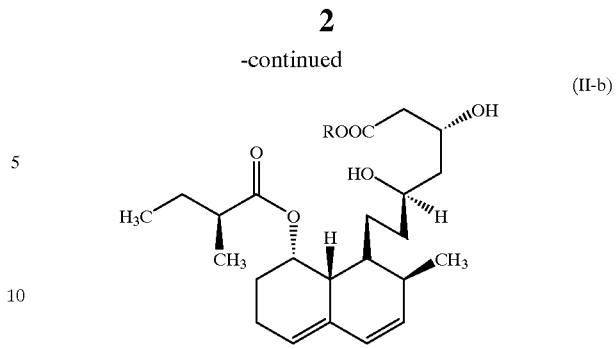

(II-b)

wherein, R is H or Na.

It was reported that *Streptomyces roseochromogenus* NRRL-1233, *Streptomyces roseochromogenus* IFO-3363, *Streptomyces roseochromogenus* IFO-3411 (U.S. Pat. No. 4,346,227) and *Streptomyces carbophilus* SANK-62585 (Ferm BP-1145), *Streptomyces halstedii* IFO-3199 (JP No. Pyung 4-349034) transformed ML-236B to pravastatin. These bacteria, however, cannot tolerate a relatively high amount of ML-236B in the culture broth because of antibacterial activity of the substrate, and show low productivity of pravastatin.

SUMMARY OF THE INVENTION

The present inventors investigated to find out a new microorganism which is tolerable to higher amount of ML-236B and also has strong transformation activity. Finally, they found a new microorganism. *Streptomyces exfoliatus* YJ-118.

DESCRIPTION OF THE DRAWINGS

The invention will be described in more detail in the drawings.

DETAILED DESCRIPTION OF THE INVENTION

Figure 1:
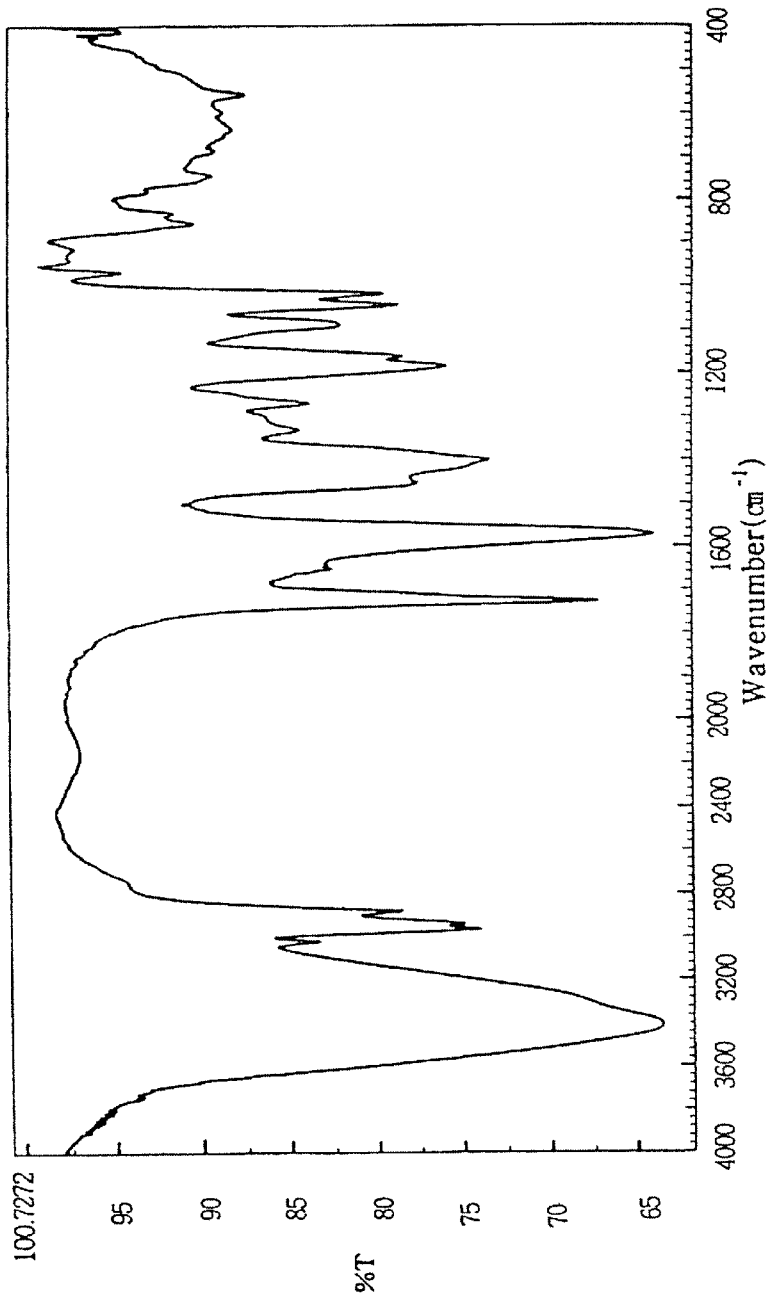
FIG. 1 is the IR spectrum of pravastatin sodium

The present inventors isolated a new microorganism, *Streptomyces exfoliatus* YJ-118. This microorganism showed strong tolerance to high amount of pravastatin precursor represented in formula II-a and formula II-b. Pravastatin known as plasma cholesterol lowering agent is produced by using this organism.

(A) Isolation of a New Microorganism

Soil samples diluted $10^{-3} \sim 10^{-5}$ fold with sterile distilled water are spread on IS No.2 agar plate containing 0.05~0.5% (w/v) ML-236B and culture at 27° C. for 7 days.

Among 500 strains isolated from the cultivation, one strain which shows strong tolerance to ML-236B and high hydroxylation activity was selected. This strain was named YJ-118.

(B) Identification of the New Microorganism

The properties of the new microorganism YJ-118 obtained from the above are as follows.

(1) Morphological Properties

YJ-118 was grown on a medium suggested by ISP (International Streptomyces Project) at 27° C. for 7~14 days. The strain has grown actively on that medium and formed substrate mycelium, aerial mycelium and spores.

Scanning electron micrograph has revealed that the surface of spore was smooth, cylindrical and the appearance of spore chain was linear or rectiflexible.

(2) Chemical Components of Strain YJ-118

Cell wall of type of YJ-118 were analyzed according to (Yamada et al., Gen. Appl. Microbiol. 16: 103–113, 1970).

L.L-diaminopimelic acid, glutamic acid, alanine were discovered and so it was proved that YJ-118 cell wall could be assigned to Type 1.

Sugar pattern in YJ-118 cells were analyzed according to (M. P. Lechavalier et al., Journal of Laboratory and clinical medicine, 71, 934 (1968)) and abnormal patterns were not shown.

The results obtained from the above have proved that the isolated microorganism from this invention belongs to genus Streptomyces.

(3) Numerical Identification of the New Streptomyces Strain 50 taxonomic unit characters of the strain for assigning to Major clusters and 34 unit characters for Minor clusters were tested in the way suggested by William et al. and the data were analyzed numerically using TAXON program. TAXON program is devised by Dr. Alan Ward[Department of Microbiology, Newcastle upon Tyne University, UK]. The data are input in the form of + or − and analyzed by CLUSTAN and numerically classified. On the basis of the numeric classification, probabilistic identification matrix is formed. By comparing the characteristics of probabilistic identification matrix with that of unidentified Streptomyces strain, the numeric identification was accomplished [Journal of general Microbiology(1983), 129, 1743~1813; Rho.Y. T, Ph. D. Thesis, Seoul National Univ(1993)].

54 unit characters of YJ-118 needed to identify this strain are shown in the following Table 1a and Table 1b.

TABLE 1a

| | Unit characters | | YJ-118 |
|---|---|---|---|
| Morphology and Pigmentation | Spore chain morphology | rectiflexible | + |
| | | spiral | − |
| | Color of sporemass | red | − |
| | | grey | + |
| | Mycelial pigment | red/orange | − |
| | Diffusive pigment | production | + |
| | | yellow/brown | + |
| | Melanin production on | PYI medium | + |
| | | Tyrosine medium | + |
| Antimicrobial activity | Bacillus subtilis | | − |
| | Micrococcus luteus | | − |
| | Candida albicans | | − |
| | Saccharomyces cerevisiae | | − |
| | Streptomyces murinus | | − |
| | Aspergillus niger | | + |
| Biochemical test | Lecithinase | | + |
| | Lipolysis | | + |
| | Pectin hydrolysis | | + |
| | Nitrate reduction | | + |
| | H₂S production | | + |
| | Hippurate reduction | | − |
| Degradation test | Elastin | | + |
| | Xanthine | | + |
| | Albutin | | + |

TABLE 1b

| | Unit characters | YJ-118 |
|---|---|---|
| Antibiotic resistance | Neomycin | − |
| | Rifampicin | − |
| | Oleandomycin | + |
| | Penicillin G | + |
| Growth test | 45° C. | − |
| | NaCl | − |
| | Sodium azide | − |
| | Phenol | − |

TABLE 1b-continued

| | Unit characters | YJ-118 |
|---|---|---|
| Compound as sole source of nitrogen | Potassium tellurite | − |
| | Thallus acetate | − |
| | DL-α-amino-n-butyric acid | + |
| | L-Cysteine | + |
| | L-Valine | + |
| | L-phenylalanine | + |
| | L-histidine | + |
| | L-Hydroxyproline | + |
| Organic compound as sole source of carbon | Sucrose | − |
| | meso-Inositol | − |
| | Mannitol | − |
| | L-Rhamnose | − |
| | Raffinose | − |
| | D-Melizitose | + |
| | Adonitol | + |
| | Dextran | − |
| | D-Melibiose | + |
| | Xylitol | − |

Identification scores of the isolated Streptomyces YJ-118 to the major clusters of Streptomyces by TAXON program are represented in Table 2.

TABLE 2

| Taxon major clusters | Taxon distance | 90% TAXON radius | Probability of strain further away (%) | Willcox probability |
|---|---|---|---|---|
| 5 | 0.3838 | 0.44554 | 48.4519 | 0.999999 |
| 6 | 0.4614 | 0.4126 | 0.1274 | 0.000000 |
| 33 | 0.4721 | 0.3955 | 0.0050 | 0.000000 |
| 1C | 0.4723 | 0.3883 | 0.0016 | 0.000000 |
| 1B | 0 5252 | 0.4404 | 0.0053 | 0.000000 |

Consequently, the isolated YJ-118 showed the highest Willcox probability to Major cluster 5 represented by *Streptomyces exfoliatus*. YJ-118 was compared with 18 strains assigned to Major cluster 5 by simple matching coefficient. The isolate YJ-118 shared only 40% similarity with *Streptomyces nashvillensis* among 18 strains.

So, this inventors named the new isolated microorganism as *Streptomyces exfoliatus* YJ-118. This strain was accepted by international depositary authority, Korea Research Institute of Bioscience and Biotechnology Korean Collection for Type Cultures and given the accession number KCTC 0318BP on Feb. 7, 1997.

*Streptomyces exfoliatus* YJ-118 has not yet been used to produce pravastatin. The present inventors used this strain to produce pravatatin sodium. Transformed *Streptomyces exfoliatus* YJ-118 by mutation and DNA recombination may be also used to produce pravastatin.

A method for producing pravastatin sodium using *Streptomyces exfoliatus* YJ-118 is described below in detail.

For the seed culture, a medium(I) containing glucose 0.5~3%, yeast extract 1.0~3.0%, beef extract 0.1~1.0%, Casein hydrolyte (N-Z amine A) 0.5~2.0% is prepared. To medium(I) is added 0.01~0.05% (w/v) ML-236B represented in formula II-a and formula II-b which is sterilized by filtration. *Streptomyces exfoliatus* YJ-118 is inoculated in medium(I) and cultured at 27° C. for 23 days. ML-236B added to the seed culture medium(I) is thought to play a role as an activator of enzymatic hydroxylating reaction. More than 0.05% (w/v) of the concentration of ML-236B in broth, however, the preculture time increased and cell growth is not good.

Ten percent of seed culture is inoculated in a production medium(II) containing glucose 1.0~3.0%, yeast extract 0.5~2.0%, polypeptone 0.1~2.0%, $K_2HPO_4$ 0.01~0.5%, $MgSO_1 \cdot 7H_2O$ 0.01~0.1%, NaCl 0.01~0.1% and cultures at 27° C. on a rotary shaker.

0.1~50% (w/v) of ML-236B, preferentially 0.1~3.0% (w/v), is added to the culture broth and the cultivation was continued at 27° C. Two or three days later, 0.3~0.5% (w/v) glucose solution was fed. It supposed that additive glucose might be used in hydroxylation of ML-236B as an energy source and a catalyst. During production culture, ML-236B concentration might be maintained in a range of 0.1~5.0%. Lower than 0.1%, pravastatin productivity decreases and higher than 5.0%, cell growes very slowly and pravastatin productivity also decreases.

It has been reported that microorganisms producing pravastatin could be tolerant to the range of 0.05~-0.1% (w/v) ML-236B concentration in culture broth. However, *Streptomyces exfoliatus* YJ-118 isolated from this invention showes tolerance to 5% (w/v) ML-236B concentration.

For the purification of pravastatin sodium, the culture broth was centrifuged and cell mass was discarded. The supernatant was adsorbed to a column of polymeric adsorbent resin and washed with water. Pravastatin sodium is eluted with 20~50% acetone solution or methanol solution. Pravastatin sodium fraction is concentrated in vacuo. The residue is applied to HPLC of ODS reverse phase and active fraction of pravastatin sodium is dried in vacuo. Pravastatin sodium is obtained as white crystal in ethanol and ethyl acetate.

The present invention is represented in detail by the examples below, which are provided only to exemplify the invention.

MANUFACTURING EXAMPLE

Soil samples collected from all around South Korea were diluted $10^{-3} \sim 10^{-5}$ fold with sterile distilled water and spread on ISP No.2 agar plates containing 0.05~0.5% (w/v) pravastatin precursor. ML-236B, represented in formula II-b.

Cultivation was done at 27° for 5~10 days. About 500 pure isolates were obtained and inoculated in 125 ml Erlenmeyer flask containing 20 ml Bennett's medium and cultured at 27° C. for 5 days on a rotary shaker. Two days later, 0.05% ML-236B was added and the cultivation was continued for 2 more days. The amount of pravastatin sodium produced from culture broth was analyzed by HPLC. Among 10 strains showing hydroxylation activity of ML-236B, one strain which had strong tolerance to ML-236B was selected and named *Streptomyces exfoliatus* YJ-118.

EXAMPLE 1

To 125 ml Erlenmeyer flask containing 20 ml seed culture medium(I) that comprises glucose 1%, yeast extract 0.2%, skim milk 0.2%, casein hydrolyte (N-Z amine) 0.5%, pH 7.0. 0.02% (w/v) ML-236B was added and *Streptomyces exfoliatus* YJ-118 isolated from manufacturing Example was inoculated. The cultivation was done at 27° C., 200 rpm, for 2 days on a rotary shaker. 20 ml of seed culture above was inoculated in 2 l Erlenmeyer flask containing 400 ml production medium(II) that comprises glucose 1.0%, yeast extract 1.0%, polypeptone 0.5%. $K_2HPO_4$ 0.1%, $MgSO_4 \cdot 7H_2O$ 0.05%, NaCl 0.01~0.1%, pH 7.2 and the flask was cultured at 27° C., 150 rpm. One day after cultivation, 0.05% (w/v) ML-236B (formula II-a) was added every day till the final concentration of ML-236B in culture broth became 0.2% (w/v). The cultivation was continued at 27° C., 150 rpm for 6 days and 0.3% glucose was fed once every two days 2 times in total. After then, the culture broth was adjusted to pH 9.0 and stirred for 3 hr. After centrifugation cell mass was removed and the supernatant was applied to a column of HP-20 500 ml. After washed with water, pravastatin sodium was eluted with 25% acetone solution. Pravastatin sodium fraction was concentrated in vacuo and the residue was applied to semi preparative HPLC(Kromasil $C_{18}$ resin). Pravastatin sodium was eluted with 35% acetonitrile solution and was obtained as white crystal 1,254 mg (627 mg/l),

EXAMPLE 2

Except for that 12 hr, after the cultivation, 0.04% (w/v) ML-236B represented in formula II-b was added to culture broth once every 12 hr, pravastatin sodium was produced from the same method as described in above Example 1. The cultivation was done at 27° C. 150 rpm for 7 days. As a result, pravastatin sodium was obtained 2.68 g (1,340 mg/l),

EXAMPLE 3

Except for that ML-236B was not added in seed culture, pravastatin sodium was produced from the same method as described above in Example 1. The obtained pravastatin sodium was 778 mg (389 mg/l). This amount of pravastatin sodium was 60–65% higher than that of other microorganisms.

COMPARATIVE EXAMPLE

U.S. Pat. No. 4,346,227

*Streptomyces roseochromogenus* NRRL 1233 was inoculated in twenty 500 ml flask containing 100 ml medium that comprises glucose 2.0%, corn steep liquor 0.2%, $K_2HPO_4$ 0.15%, yeast extract 0.1%, $MgSO_4 \cdot 7H_2O$ 0.15%, $ZnSO_4 \cdot 7H_2O$ 0.001%, $NH_4NO_3$ 0.1%, peptone 0.1% .pH 7.0 and cultured at 26° C., 120 rpm for 2 days on a rotary shaker. 0.05% (w/v) ML-236B represented in formula II-b was added to the culture broth, 2 days after cultivation. After cultivation was done for 5 days, 120 mg (60 mg/l) pravastatin sodium was obtained from the method described above in Example 1.

Considering ML-236B concentration in culture broth -and pravastatin productivity, the present invention is more excellent than Comparative Example described above.

EXPERIMENTAL EXAMPLE

The physical properties of pravastatin sodium obtained from Example 1 and Comparative Example are described in Table 3.

TABLE 3

| Article | EXAMPLE 1 | COMPARATIVE EXAMPLE |
|---|---|---|
| Formula | $C_{23}H_{35}O_7Na$ | $C_{23}H_{35}O_7Na$ |
| Molecular weight | 446.52 | 446.52 |
| UV spectrum (MeOH) | 230, 237, 245 nm | 230, 237, 245 nm |
| IR spectrum ($cm^{-1}$ · KBr) | 3415, 2964, 2935, 2875, 1727, 1578, 1402, 1265, 1184, 1157, 1085, 1043, 1015, 854, 557, 421 | 2960, 2930, 2875, 1725, 1400, 1330, 1300, 1265, 1180, 1160, 1080, 1045, 1015, 965 |
| Specific rotation $[\alpha]^{26}$ | +150~160° | +150~160° |

Figure 2:
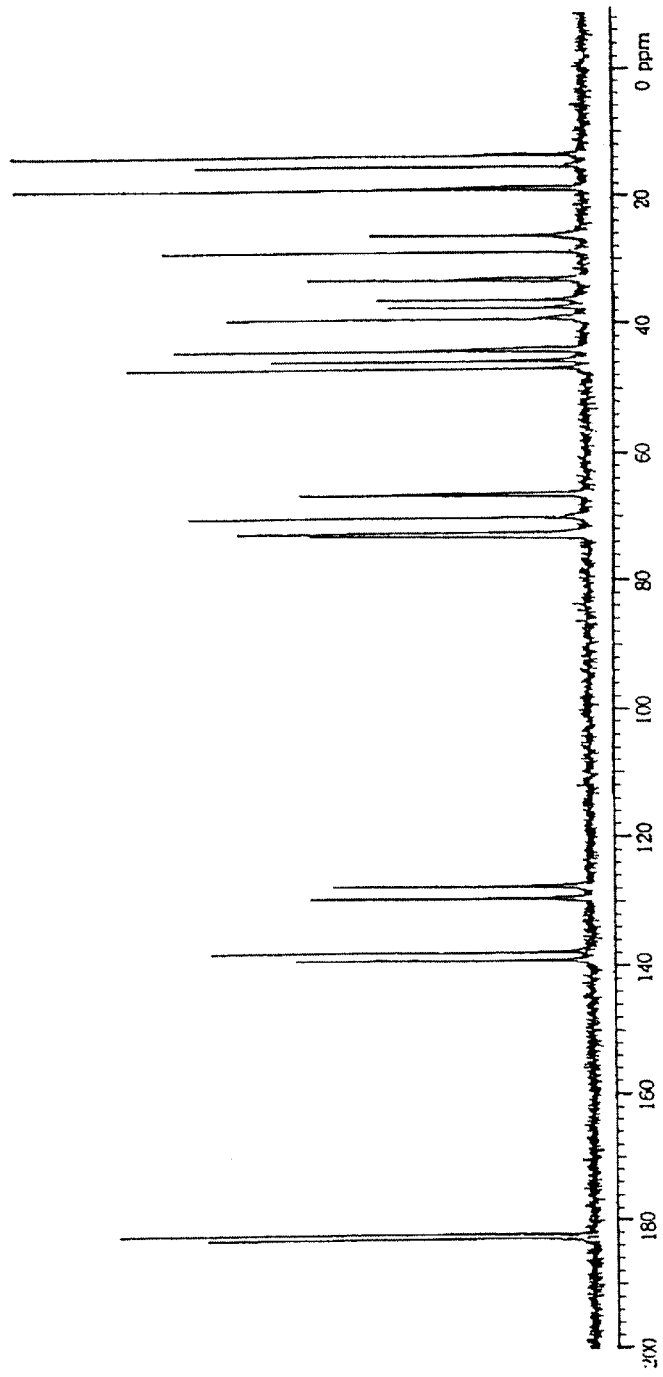
FIG. 2 is the $^{13}$C-NMR spectrum of pravastatin sodium
Figure 3:
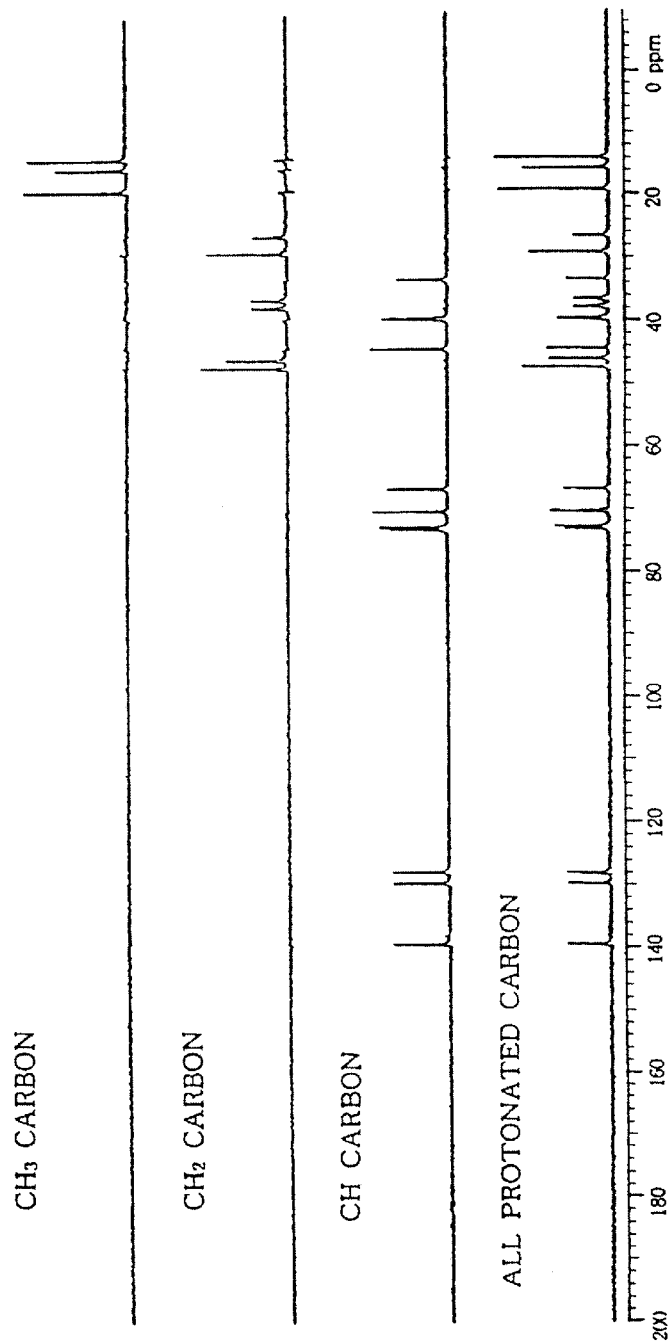
FIG. 3 is the $^1$H-NMR spectrum of pravastatin sodium

IR spectrum, $^{13}C$-NMR spectrum, $^{1}H$-NMR spectrum of pravastatin sodium obtained from this invention are represented in FIG. 1, FIG. 2 and FIG. 3. respectively.

By using a new microorganism *Streptomyces exfoliatus* YJ-118 isolated from this invention, ML-236B concentration in culture broth could be raised to 0.5% (w/v) and pravastatin sodium productivity was increased up to 600~1,340 mg/l much higher than that of other microorganisms(60 mg/l).

What is claimed is:

1. An isolated *Streptomyces exfoliatus* YJ-118.

2. A method for producing pravastatin sodium represented in formula I comprising culturing *Streptomyces exfoliatus* YJ-118 in the presence of ML-236B represented in formula II-a and formula II-b and allowing the *Streptomyces exfoliatus* YJ-118 to hydroxylate the ML-236B represented in formula II-a and formula II-b;

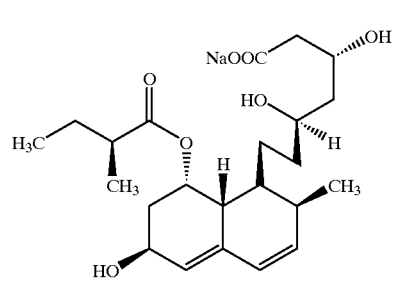
(I)

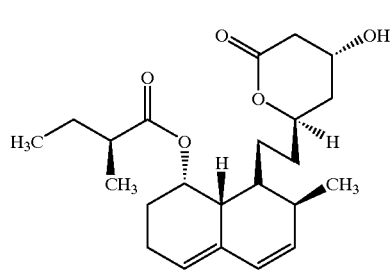
(II-a)

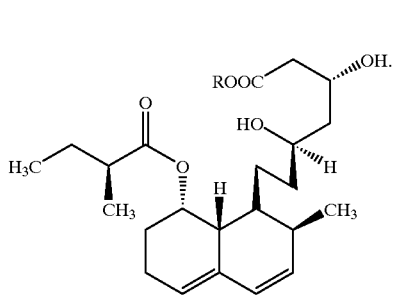
(II-b)

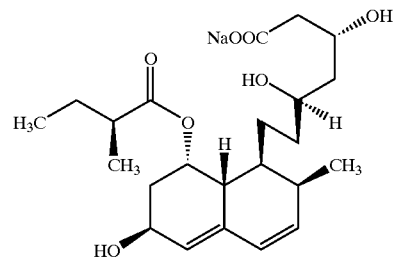
(I)

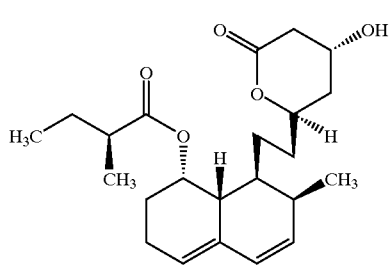
(II-a)

3. The method for producing pravastatin sodium according to claim 2, wherein the *Streptomyces exfoliatus* YJ-118 is cultured in a seed culture medium containing less than 0.05% (w/v) ML-236B.

4. The method for producing pravastatin sodium according to claim 2, wherein the *Streptomyces exfoliatus* YJ-118 is cultured in a production medium containing 0.1 to 5.0% (w/v) ML-236B.

* * * * *

UNITED STATES PATENT AND TRADEMARK OFFICE
CERTIFICATE OF CORRECTION

PATENT NO. : 6,306,629 B1
DATED : October 23, 2001
INVENTOR(S) : Lee et al.

It is certified that error appears in the above-identified patent and that said Letters Patent is hereby corrected as shown below:

<u>Column 7,</u>
Lines 36-60, please delete formulas (I) and (II-a).

Signed and Sealed this

Second Day of July, 2002

*Attest:*

*Attesting Officer*

JAMES E. ROGAN
*Director of the United States Patent and Trademark Office*